United States Patent [19]

Nedelec

[11] Patent Number: 4,703,050
[45] Date of Patent: Oct. 27, 1987

[54] METHODS OF INDUCING NEURON PROTECTIVE ACTIVITY

[75] Inventor: Lucien Nedelec, Le Raincy, France

[73] Assignee: Roussel Uclaf, Paris, France

[21] Appl. No.: 927,751

[22] Filed: Nov. 6, 1986

[30] Foreign Application Priority Data

Nov. 13, 1985 [FR] France ............................. 85 16743

[51] Int. Cl.⁴ ........................................... A61K 31/435
[52] U.S. Cl. .................................................. 514/277
[58] Field of Search ......................................... 514/277

[56] References Cited

U.S. PATENT DOCUMENTS 3,901,894 8/1975 Kornfeld et al. ..................... 546/67

Primary Examiner—Stanley J. Friedman
Attorney, Agent, or Firm—Bierman & Muserlian

[57] ABSTRACT

A method of inducing neuron protective activity in warm-blooded animals comprising administering to warm-blooded animals an amount sufficient to induce protective activity of at least one compound of the formula

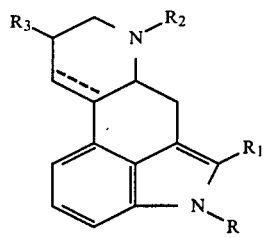

wherein R and $R_2$ are individually selected from the group consisting of hydrogen and alkyl of 1 to 4 carbon atoms, $R_1$ is selected from the group consisting of hydrogen, chlorine and bromine and $R_3$ is alkylthiomethyl of 1 to 4 alkyl carbon atoms, the dotted line indicates the optional presence of a double bond and their non-toxic, pharmaceutically acceptable acid addition salts useful for treating aged persons or persons suffering cerebral injury.

7 Claims, No Drawings

METHODS OF INDUCING NEURON PROTECTIVE ACTIVITY

STATE OF THE ART

A large number of synthetic derivatives of ergoline are known to possess dopaminergic properties such as antiprolactin, hypotensive or antihypertensive and/or antiparkinsonian activity. Examples of such patents are U.S. Pat. Nos. 3,901,894 and 4,098,790 and Belgium patent Nos. 849,318, 802,531, 811,610 and 794,888. However, there is not any relationship between dopaminergic activity and neuron protective activity.

OBJECTS OF THE INVENTION

It is an object of the invention to provide a novel method of inducing neuron protective activity in warm-blooded animals, including humans.

This and other objects and advantages of the invention will become obvious from the following detailed description.

THE INVENTION

The novel method of the invention of inducing neuron protective activity in warm-blooded animals comprises administering to warm-blooded animals an amount sufficient to induce neuron protective activity of at least one compound of the formula

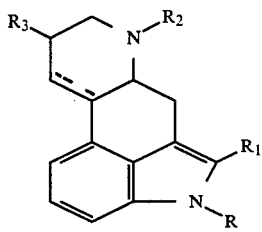

wherein R and $R_2$ are individually selected from the group consisting of hydrogen and alkyl of 1 to 4 carbon atoms, $R_1$ is selected from the group consisting of hydrogen, chlorine and bromine and $R_3$ is alkylthiomethyl of 1 to 4 alkyl carbon atoms, the dotted line indicates the optional presence of a double bond and their non-toxic, pharmaceutically acceptable acid addition salts.

In the compounds of formula I, alkyl of 1 to 4 carbon atoms, preferably methyl, ethyl, propyl or isopropyl and the alkylthiomethyl may be n-propylthiomethyl, ethylthiomethyl and preferably methylthiomethyl.

Examples of suitable acids for the non-toxic, pharmaceutically acceptable acid addition salts are mineral acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid and aspartic acid, alkane sulfonic acids such as methane sulfonic acid and ethane sulfonic acid and arylsulfonic acids such as benzene sulfonic acid and p-toluene sulfonic acids and aryl carboxylic acids such as benzoic acid.

Among the preferred compounds of formula I are those wherein the dotted line is not a second bond, those wherein R is hydrogen, those wherein $R_1$ is hydrogen and their non-toxic, pharmaceutically acceptable acid addition salts. Particularly preferred compounds are 6-methyl-8β-methylthiomethyl-9,10-didehydroergoline and 6-methyl-8β-methylthiomethyl-ergoline and their non-toxic, pharmaceutically acceptable acid addition salts.

The compounds of formula I and their non-toxic, pharmaceutically acceptable acid addition salts have a remarkable neuron protective activity making them useful for the treatment of cerebral aging or conditions connected with cerebral hypoxia.

The compounds may be administered in the usual pharmaceutical forms such as tablets, dragees, capsules, granules, suppositories and injectable solutions or suspensions. Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compounds may be administered orally, rectally or parenterally and the usual daily dose is 0.015 to 3.0 mg/kg depending on the compound, the condition treated and the method of administration. For example, product A of the Example is orally administered at 0.015 to 1.5 mg/kg for the treatment of cerebral aging.

In the following examples there are described several preferred embodiments to illustrate the invention. However it should be understood that the invention is not intended to be limited to the specific embodiments. Product A is the hydrochloride of 6-methyl-8β-(methylthiomethyl)-ergoline and product B is the hydrochloride of the corresponding 9,10-didehydro-ergoline described in U.S. Pat. No. 3,901,894.

EXAMPLE 1

Hypobaric Anoxemia Test

Male mice weighing 20–22 g were used having eaten nothing for 5 hours and they were divided into groups of 10 animals. The product to be tested was administered to the animals subcutaneously. Fifteen minutes after the administration of the product, the animals were placed in a 2 liter dessicator in which the pressure was rapidly brought to 190 mm of Hg with a pump, and their survival time was noted in seconds. The increase in the survival time, expressed as a percentage was calculated for the treated animals in comparison with control animals submitted to the same conditions. The following results were obtained.

| Product | Doses in mg/kg | % Increase in the survival time |
|---------|----------------|-------------------------------|
| A       | 1              | +12%                          |
|         | 10             | +57%                          |

EXAMPLE 2

Enolase Test

Injured cerebral cells release enolase γγ which is a specific indicator of neuron lesion. In this test, the lesions were induced in the mice by sub-cutaneous injection of 35 mg/kg of kainic acid. Product A administered intraperitoneally at a dose of 1 mg/kg, 1 hour before the injection of the neurotoxin decreased the serous concentration of enolase by 29% which means the product protected the cerebral cells in the affected area.

EXAMPLE 3

Acute Toxicity Study

The lethal dose $LD_0$ of product A was evaluated after oral administration to mice and the maximum dose which did not cause mortality in 8 days is called the $LD_0$. The result obtained was $LD_0$ in mg/kg $=200$.

EXAMPLE 4

Asphysic Anoxemia Test

Curare was administered to mice which were placed under assisted respiration and the products to be tested were administered at a dose of 2 mg/kg, and the respiratory assistance was stopped. The increase in the time necessary for the electroencephalogram to disappear was noted in comparison with the control animals and the results are the following:

| Product | Administration observed |
|---------|------------------------|
| A | +10% |
| B | +11% |

Products A and B prolong the electro-encephalographic survival in the animals which have been treated.

Various modifications of the method of the invention may be made without departing from the spirit or scope thereof and it is to be understood that the invention is intended to be limited only as defined in the appended claims.

What I claim is:

1. A method of inducing neuron protective activity in warm-blooded animals comprising administering to a warm-blooded animal requiring neuron protective activity an amount sufficient to induce neuron protective activity of at least one compound of the formula

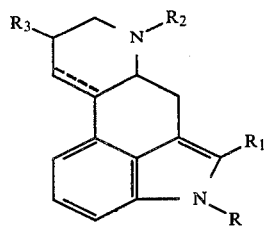

wherein R and $R_2$ are individually selected from the group consisting of hydrogen and alkyl of 1 to 4 carbon atoms, $R_1$ is selected from the group consisting of hydrogen, chlorine and bromine and $R_3$ is alkylthiomethyl of 1 to 4 alkyl carbon atoms, the dotted line indicates the optional presence of a double bond and a non-toxic, pharmaceutically acceptable acid addition salt.

2. The method of claim 1 wherein the dotted line is not a double bond.
3. The method of claim 1 wherein R is hydrogen.
4. The method of claim 1 wherein $R_1$ is hydrogen.
5. The method of claim 2 wherein R and $R_1$ are hydrogen.
6. The method of claim 1 wherein the active compound is selected from the group consisting of 6-methyl-8β-methylthiomethyl-ergoline and its non-toxic, pharmaceutically acceptable acid addition salt.
7. The method of claim 1 wherein the active compound is selected from the group consisting of 6-methyl-8β-methylthiomethyl-ergoline and its non-toxic, pharmaceutically acceptable acid addition salt.

* * * * *